(12) United States Patent
Magee

(10) Patent No.: US 10,932,785 B2
(45) Date of Patent: Mar. 2, 2021

(54) EXPANDABLE MEMBER FOR PERFORATION OCCLUSION

(71) Applicant: The Spectranetics Corporation, Colorado Springs, CO (US)

(72) Inventor: Matthew Myles Magee, Monument, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 206 days.

(21) Appl. No.: 15/174,045

(22) Filed: Jun. 6, 2016

(65) Prior Publication Data

US 2016/0278783 A1    Sep. 29, 2016

Related U.S. Application Data

(63) Continuation of application No. 13/801,659, filed on Mar. 13, 2013, now Pat. No. 9,358,042.

(51) Int. Cl.
*A61B 17/12* (2006.01)
*A61M 25/10* (2013.01)
(Continued)

(52) U.S. Cl.
CPC .... *A61B 17/12036* (2013.01); *A61B 17/1204* (2013.01); *A61B 17/12109* (2013.01);
(Continued)

(58) Field of Classification Search
CPC .......... A61B 17/3468; A61B 17/12036; A61B 17/12022; A61B 17/12027;
(Continued)

(56) References Cited

U.S. PATENT DOCUMENTS 3,834,394 A    9/1974 Hunter et al.
4,413,989 A    11/1983 Schjeldahl et al.
(Continued)

FOREIGN PATENT DOCUMENTS

EP    0760688 B1    11/2001
EP    0981387 B1    11/2003
(Continued)

OTHER PUBLICATIONS

International Search Report and Written Opinion issued in PCT/US2014/019274 dated Jun. 3, 2014. 14 pages.
(Continued)

*Primary Examiner* — Diane D Yabut
*Assistant Examiner* — Christian D Knauss

(57) ABSTRACT

Lead extraction is the removal of one or more leads from inside the heart utilizing a lead removal catheter having a tubular sheath that is placed in the blood vessel, either subclavian or femoral. The sheath of the lead removal catheter may accidentally tear or perforate the blood vessel as it is advanced over the lead toward the heart. Such an occurrence must be dealt with quickly to prevent harm to the patient or subject. An expandable member, such as a balloon, attached to the exterior of the sheath of a lead removal catheter can be deployed temporarily adjacent the perforation in the vessel wall. Inflation of the balloon not only stops (or substantially stops) the bleeding, but, upon inflation, the balloon may include one or more channels that allow blood to continue to flow through the channel(s) until the blood vessel perforation can be repaired.

7 Claims, 2 Drawing Sheets

(51) Int. Cl.
*A61B 17/34* (2006.01)
*A61N 1/05* (2006.01)

(52) U.S. Cl.
CPC .... *A61B 17/12136* (2013.01); *A61B 17/3468* (2013.01); *A61M 25/10* (2013.01); *A61M 25/1002* (2013.01); *A61N 1/0587* (2013.01)

(58) Field of Classification Search
CPC .......... A61B 17/1204; A61B 17/12099; A61B 17/12136; A61B 17/12109; A61B 17/12122; A61B 17/12131; A61M 25/10; A61M 25/1002; A61N 1/0587; A61N 1/056; A61N 2001/0578
See application file for complete search history.

(56) References Cited

U.S. PATENT DOCUMENTS

| | | | |
|---|---|---|---|
| 4,545,390 | A | 10/1985 | Leary |
| 4,689,041 | A | 8/1987 | Corday et al. |
| 4,836,204 | A | 6/1989 | Landymore et al. |
| 5,108,370 | A * | 4/1992 | Walinsky ............ A61M 25/104 604/102.02 |
| 5,273,536 | A | 12/1993 | Savas |
| 5,304,121 | A | 4/1994 | Sahatjian |
| 5,330,528 | A * | 7/1994 | Lazim ...................... A61F 2/07 606/194 |
| 5,338,298 | A | 8/1994 | McIntyre |
| 5,358,487 | A | 10/1994 | Miller |
| 5,383,856 | A | 1/1995 | Bersin |
| 5,417,689 | A | 5/1995 | Fine |
| 5,439,445 | A | 8/1995 | Kontos |
| 5,447,497 | A | 9/1995 | Sogard et al. |
| 5,470,313 | A | 11/1995 | Crocker et al. |
| 5,470,314 | A * | 11/1995 | Walinsky .......... A61M 25/1002 604/103.11 |
| 5,496,311 | A | 3/1996 | Abele et al. |
| 5,540,679 | A | 7/1996 | Fram et al. |
| 5,554,119 | A * | 9/1996 | Harrison ........... A61M 25/1002 604/101.05 |
| 5,599,306 | A | 2/1997 | Klein et al. |
| 5,613,948 | A * | 3/1997 | Avellanet ......... A61M 25/1002 604/103.07 |
| 5,759,170 | A | 6/1998 | Peters |
| 5,766,151 | A | 6/1998 | Valley et al. |
| 5,795,331 | A * | 8/1998 | Cragg .............. A61B 17/12022 604/103.01 |
| 5,800,393 | A | 9/1998 | Sahota |
| 5,820,595 | A | 10/1998 | Parodi |
| 5,823,996 | A | 10/1998 | Sparks |
| 5,843,027 | A * | 12/1998 | Stone ...................... A61F 2/958 604/509 |
| 5,843,116 | A | 12/1998 | Crocker et al. |
| 5,865,787 | A | 2/1999 | Shapland et al. |
| 5,885,244 | A | 3/1999 | Leone et al. |
| 5,985,307 | A | 11/1999 | Hanson et al. |
| 6,059,823 | A * | 5/2000 | Holman ........... A61B 17/12045 623/1.15 |
| 6,071,271 | A | 6/2000 | Baker et al. |
| 6,139,517 | A * | 10/2000 | Macoviak ........ A61M 25/1002 604/101.05 |
| 6,159,197 | A | 12/2000 | Heuser |
| 6,176,821 | B1 | 1/2001 | Crocker et al. |
| 6,221,043 | B1 | 4/2001 | Fischell et al. |
| 6,258,019 | B1 | 7/2001 | Verin et al. |
| 6,293,924 | B1 | 9/2001 | Bagaoisan et al. |
| 6,315,757 | B1 | 11/2001 | Chee et al. |
| 6,346,092 | B1 | 2/2002 | Leschinsky |
| 6,458,069 | B1 | 10/2002 | Tam et al. |
| 6,461,327 | B1 | 10/2002 | Addis et al. |
| 6,485,500 | B1 | 11/2002 | Kokish et al. |
| 6,491,663 | B1 | 12/2002 | Lemelson |
| 6,506,180 | B1 * | 1/2003 | Lary ................... A61M 25/104 604/101.04 |
| 6,540,721 | B1 | 4/2003 | Voyles et al. |
| 6,572,633 | B1 | 6/2003 | Löffler et al. |
| 6,579,847 | B1 | 6/2003 | Unger |
| 6,613,066 | B1 | 9/2003 | Fukaya et al. |
| 6,616,629 | B1 | 9/2003 | Verin et al. |
| 6,623,504 | B2 | 9/2003 | Vrba et al. |
| 6,626,861 | B1 | 9/2003 | Hart et al. |
| 6,629,952 | B1 | 10/2003 | Chien et al. |
| 6,645,167 | B1 | 11/2003 | Whalen, II et al. |
| 6,652,441 | B2 | 11/2003 | Weinberger et al. |
| 6,652,485 | B1 | 11/2003 | Gaudoin et al. |
| 6,656,153 | B1 | 12/2003 | Sakai et al. |
| 6,663,614 | B1 | 12/2003 | Carter |
| 6,679,900 | B2 | 1/2004 | Kieturakis et al. |
| 6,682,545 | B1 | 1/2004 | Kester |
| 6,699,170 | B1 | 3/2004 | Crocker et al. |
| 6,706,010 | B1 | 3/2004 | Miki et al. |
| 6,723,070 | B1 | 4/2004 | Arai et al. |
| 6,743,208 | B1 | 6/2004 | Coyle |
| 6,743,227 | B2 | 6/2004 | Seraj et al. |
| 6,875,209 | B2 | 4/2005 | Zvuloni et al. |
| 6,902,571 | B2 | 6/2005 | Owens et al. |
| 6,936,057 | B1 * | 8/2005 | Nobles ............. A61B 17/12036 606/194 |
| 6,939,057 | B2 * | 9/2005 | Beier .................... G02B 6/421 385/89 |
| 6,955,658 | B2 | 10/2005 | Murray et al. |
| 6,960,186 | B1 | 11/2005 | Fukaya et al. |
| 7,137,395 | B2 | 11/2006 | Fried et al. |
| 7,169,140 | B1 | 1/2007 | Kume |
| 7,232,452 | B2 | 6/2007 | Adams et al. |
| 7,247,147 | B2 | 7/2007 | Nishide et al. |
| 7,306,575 | B2 | 12/2007 | Barbut et al. |
| 7,322,959 | B2 | 1/2008 | Warnack et al. |
| 7,402,172 | B2 | 7/2008 | Chin et al. |
| 7,491,188 | B2 | 2/2009 | Holman et al. |
| 7,645,290 | B2 | 1/2010 | Lucas |
| 7,722,568 | B2 | 5/2010 | Lenker et al. |
| 7,727,228 | B2 | 6/2010 | Abboud et al. |
| 7,862,575 | B2 | 1/2011 | Tal |
| 7,862,577 | B2 | 1/2011 | Gray et al. |
| 7,909,794 | B2 | 3/2011 | Briscoe et al. |
| 7,931,663 | B2 | 4/2011 | Farnan et al. |
| 7,942,850 | B2 | 5/2011 | Levit et al. |
| 8,021,386 | B2 | 9/2011 | Davidson et al. |
| 8,177,779 | B2 | 5/2012 | Joye et al. |
| 8,221,342 | B2 | 7/2012 | Mesallum |
| 8,231,617 | B2 | 7/2012 | Satake |
| 8,235,941 | B2 | 8/2012 | Hayman et al. |
| 8,292,913 | B2 | 10/2012 | Warnack et al. |
| 8,323,307 | B2 | 12/2012 | Hardert |
| 8,348,890 | B2 | 1/2013 | Gerrans et al. |
| 8,372,034 | B2 | 2/2013 | Levit et al. |
| 8,382,787 | B2 | 2/2013 | Burton et al. |
| 8,414,611 | B2 | 4/2013 | Chalekian |
| 8,518,105 | B2 | 8/2013 | Hossainy et al. |
| 8,563,510 | B2 | 10/2013 | Hakimimehr et al. |
| 8,574,225 | B2 | 11/2013 | Reynolds |
| 8,667,838 | B2 | 3/2014 | Hoem et al. |
| 8,708,996 | B2 | 4/2014 | Consigny et al. |
| 8,740,961 | B2 | 6/2014 | Fulton et al. |
| 8,784,602 | B2 | 7/2014 | Schaeffer et al. |
| 8,801,662 | B2 | 8/2014 | Doshi et al. |
| 8,852,146 | B2 | 10/2014 | Horn et al. |
| 8,864,705 | B2 | 10/2014 | Nishigishi |
| 8,936,568 | B2 | 1/2015 | Webler et al. |
| 8,986,339 | B2 | 3/2015 | Warnack et al. |
| 9,044,580 | B2 | 6/2015 | Freyman et al. |
| 9,173,817 | B2 | 11/2015 | Sharma et al. |
| 9,358,042 | B2 | 6/2016 | Magee |
| 9,504,807 | B2 | 11/2016 | Drasler et al. |
| 9,522,215 | B2 | 12/2016 | Rago et al. |
| 9,579,449 | B2 | 2/2017 | Sharma et al. |
| 2002/0010411 | A1 * | 1/2002 | Macoviak .......... A61M 25/1002 604/8 |
| 2002/0133217 | A1 * | 9/2002 | Sirhan .................... A61M 25/10 623/1.11 |
| 2003/0004462 | A1 * | 1/2003 | Halpin ............... A61B 17/0057 604/99.04 |

(56) References Cited

U.S. PATENT DOCUMENTS

| | | |
|---|---|---|
| 2003/0050660 A1 | 3/2003 | Hackett |
| 2003/0060782 A1* | 3/2003 | Bose ................ A61B 17/12022 604/265 |
| 2003/0163154 A1 | 8/2003 | Miyata et al. |
| 2003/0199914 A1 | 10/2003 | Diaz |
| 2004/0006305 A1 | 1/2004 | Hebert et al. |
| 2004/0122362 A1 | 6/2004 | Houser et al. |
| 2004/0215310 A1* | 10/2004 | Amirana ................ A61B 18/14 623/1.11 |
| 2004/0249243 A1 | 12/2004 | Kleiner |
| 2004/0267196 A1 | 12/2004 | Miki et al. |
| 2005/0015047 A1 | 1/2005 | Shah |
| 2005/0033263 A1 | 2/2005 | Gottlieb et al. |
| 2005/0075711 A1 | 4/2005 | Neary |
| 2005/0209674 A1 | 9/2005 | Kutscher et al. |
| 2006/0095065 A1 | 5/2006 | Tanimura et al. |
| 2006/0173298 A1 | 8/2006 | Tucker |
| 2006/0258981 A1 | 11/2006 | Eidenschink |
| 2007/0203453 A1 | 8/2007 | Mori et al. |
| 2008/0132836 A1* | 6/2008 | Burton ................ A61M 25/10 604/103.08 |
| 2008/0177228 A1* | 7/2008 | Burton ............. A61M 25/1029 604/103.06 |
| 2008/0287907 A1 | 11/2008 | Gregory et al. |
| 2009/0054922 A1 | 2/2009 | Broker |
| 2009/0076447 A1 | 3/2009 | Casas et al. |
| 2009/0105686 A1 | 4/2009 | Snow et al. |
| 2009/0131785 A1 | 5/2009 | Lee et al. |
| 2009/0192452 A1 | 7/2009 | Sasajima et al. |
| 2009/0306700 A1 | 12/2009 | Miyata et al. |
| 2010/0004623 A1 | 1/2010 | Hamilton et al. |
| 2010/0016833 A1* | 1/2010 | Ogle ................ A61B 17/12022 604/509 |
| 2010/0100105 A1* | 4/2010 | Bates ........................ A61F 2/04 606/114 |
| 2010/0185220 A1 | 7/2010 | Naghavi et al. |
| 2010/0324648 A1 | 12/2010 | Scheller et al. |
| 2011/0082465 A1* | 4/2011 | Verma ................ A61B 17/1204 606/129 |
| 2011/0190727 A1 | 8/2011 | Edmunds et al. |
| 2011/0190867 A1 | 8/2011 | Vonderwalde et al. |
| 2011/0202016 A1 | 8/2011 | Zugates et al. |
| 2012/0040137 A1 | 2/2012 | Palasis et al. |
| 2012/0107439 A1 | 5/2012 | Sharma et al. |
| 2012/0109177 A1 | 5/2012 | Ulmer |
| 2012/0157987 A1 | 6/2012 | Steinke et al. |
| 2012/0265287 A1 | 10/2012 | Sharma et al. |
| 2012/0310210 A1 | 12/2012 | Campbell et al. |
| 2013/0073025 A1 | 3/2013 | Kassab |
| 2013/0090679 A1 | 4/2013 | Hoem et al. |
| 2013/0165925 A1 | 6/2013 | Mathur et al. |
| 2013/0211381 A1 | 8/2013 | Feld |
| 2013/0310687 A1 | 11/2013 | Takizawa et al. |
| 2013/0317418 A1 | 11/2013 | Freyman et al. |
| 2014/0018732 A1 | 1/2014 | Bagaoisan et al. |
| 2014/0094893 A1 | 4/2014 | Gerber |
| 2014/0100646 A1 | 4/2014 | Hassan et al. |
| 2014/0180248 A1 | 6/2014 | Salik |
| 2014/0228745 A1 | 8/2014 | Sharma et al. |
| 2014/0249475 A1 | 9/2014 | Pacetti |
| 2014/0257181 A1 | 9/2014 | Speck |
| 2014/0257266 A1 | 9/2014 | Kasprzyk et al. |
| 2014/0277399 A1 | 9/2014 | Pacetti et al. |
| 2014/0316367 A1 | 10/2014 | Zugates et al. |
| 2015/0012031 A1 | 1/2015 | Rago et al. |
| 2015/0080875 A1 | 3/2015 | Kasprzyk et al. |
| 2015/0112256 A1 | 4/2015 | Byrne et al. |
| 2015/0223819 A1 | 8/2015 | Rago et al. |
| 2015/0224235 A1 | 8/2015 | Sharma et al. |
| 2016/0051264 A1 | 2/2016 | Freyman et al. |
| 2016/0082144 A1 | 3/2016 | Freyman et al. |
| 2016/0114125 A1 | 4/2016 | Di Caprio et al. |
| 2016/0279302 A1 | 9/2016 | Sharma et al. |
| 2017/0042519 A1 | 2/2017 | Sotak et al. |

FOREIGN PATENT DOCUMENTS

| | | |
|---|---|---|
| EP | 0853957 B1 | 6/2004 |
| EP | 1129737 B1 | 7/2005 |
| EP | 1051990 B1 | 10/2008 |
| EP | 2002779 A2 | 3/2009 |
| EP | 2331187 A2 | 9/2009 |
| EP | 2331196 A1 | 12/2009 |
| EP | 1879652 B1 | 6/2012 |
| EP | 1802368 B1 | 7/2013 |
| WO | 1994002195 A1 | 2/1994 |
| WO | 1999002202 A2 | 1/1999 |
| WO | 2004096339 A1 | 11/2004 |
| WO | 2010048729 A1 | 5/2010 |
| WO | 2010078875 A1 | 7/2010 |
| WO | 2012015623 A1 | 2/2012 |
| WO | 2012027138 A1 | 3/2012 |
| WO | 2012078612 A2 | 6/2012 |
| WO | 2014004160 A1 | 1/2014 |
| WO | 2014102611 A2 | 7/2014 |
| WO | 2014152742 A2 | 9/2014 |
| WO | 2014158687 A1 | 10/2014 |
| WO | 2015021375 A1 | 2/2015 |

OTHER PUBLICATIONS

International Search Report and Written Opinion issued in PCT/US2016/046489, dated Nov. 10, 2016, 12 pages.

U.S. Appl. No. 13/801,659, filed Mar. 13, 2013.

* cited by examiner

EXPANDABLE MEMBER FOR PERFORATION OCCLUSION

CROSS-REFERENCE TO RELATED APPLICATIONS

This application is a continuation of U.S. patent application Ser. No. 13/801,659, filed Mar. 13, 2013, now U.S. Pat. No. 9,358,042, titled EXPANDABLE MEMBER FOR PERFORATION OCCLUSION, which is hereby incorporated herein by reference in its entirety for all that it teaches and for all purposes.

FIELD

This disclosure relates generally to lead removal catheters and particularly to a lead removal catheter having an expandable member, such as a balloon, attached to thereto. The expandable member may be inflated within a patient's vascular system. Upon being inflated, the balloon creates a passageway between its interior and the sheath's exterior, thereby allowing blood to flow through the passageway.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached to the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the sear tissue surrounding the lead. In some cases, the cutting blade and sheath may also separate the tissue itself from the lead. Once the lead is separated from the surrounding tissue and/or the surrounding tissue is separated from the remaining sear tissue, the lead may be inserted into a hollow lumen of the sheath for removal and/or be removed from the patient's vasculature using some other mechanical devices, such as the mechanical traction device previously described in United States Patent Publication No. 2008/0154293 to Taylor, which is hereby incorporated herein by reference in its entirety for all that it teaches and for all purposes. Examples of a such devices and methods used to extract loads is described and illustrated in U.S. Pat. No. 5,651,781 to Grace, which is incorporated herein by reference in its entirety for all that it teaches and for all purposes.

Examples of a laser catheter assembly or laser sheaths that may be used for removing a surgically implanted lead is a coronary laser atherectomy catheter by the Spectranetics Corporation under the trade names SLSII™ and GlideLight™. FIG. 5 depicts the distal end of a flexible catheter 50 comprising multiple fiber optic laser emitters 58 surrounding a lumen 54. As the fiber optic laser emitters 58 cut the tissue surrounding the lead, the sheath slides over the lead and surrounding tissue, which enter the lumen.

Lead extraction is generally a very safe procedure. However, as with any invasive procedure, there are potential risks. For example, while using any of the tools discussed above to remove a lead, the tool may accidentally pierce, cut, or perforate the vein or artery through which the tool is traveling, thereby allowing blood to escape the patient's vascular system. The rate at which blood escapes, may be high if the accidental opening is created close to the patient's heart. Accordingly, a clinician must address the situation quickly to mitigate the amount of blood that escapes from the patient, thereby minimizing potential long-term harm to the patient.

SUMMARY

These and other needs are addressed by the various aspects, embodiments, and configurations of the present disclosure. The disclosure is generally directed to the use of a (typically radially or peripherally) expandable member, such as a balloon, attached to or otherwise engaged with the exterior of the sheath of a lead removal catheter or other type of catheter. The expandable member is positioned adjacent the vascular opening that is accidentally created by the lead removal catheter. Once positioned at the opening, the expandable member can be inflated, which will permit the exterior of the expandable member to press against or otherwise contact the opening and stop, or at least substantially minimize the bleeding. Upon expansion (e.g., inflation), a passageway is created through the interior of the expandable member, thereby allowing blood to flow from one side of the expandable member to the other and through the patient's vasculature system until the opening can be repaired. Typically, a clinician or surgeon will institute a separate procedure to surgically repair the site.

A method, according to this disclosure, can occlude an opening in as patient's vascular system by the steps of:
(a) advancing a sheath in a blood vessel until an expandable member engaged with the sheath is positioned at least substantially adjacent an opening in the blood vessel; and
(b) expanding the expandable member, thereby at least substantially eluding the opening.

A device, according to the disclosure, can include:
(a) a catheter sheath having an outer surface; and
(b) an expandable member attached to the sheath, the expandable member comprising an interior surface and an exterior surface wherein the expandable member is capable of being expanded and, upon expansion, a channel is formed between the interior surface of the expandable member and the outer surface of the sheath.

A radially expandable member according to this disclosure, can include:
(a) a radially expandable member comprising an annulus for receiving a sheath of a catheter;
(b) at least two flexible connecting members for connecting the radially expandable member to the sheath; and
(c) at least two channels bound by an inner surface of the expandable member, an outer surface of the sheath, and the two or more flexible connecting members.

Blood can continue to flow through the blood vessel, by means of the channel, until the opening (e.g., perforation) can be repaired.

The expandable member can be an inflatable and deflatable balloon.

The cross section of the channel can be at least substantially eccentrically shaped.

The expandable member, when expanded, can be at least substantially cylindrical, and the sheath can be positioned in an annulus of the expandable member.

The expandable member can include and/or release a coagulant to facilitate blood clotting in the opening of the blood vessel.

In one procedure, as the sheath of a lead removal catheter is advanced over a lead, and the blood vessel is accidentally perforated by the tip of the sheath, the perforation can be detected with a fluoroscopic device, through monitoring blood pressure or any other suitable method or means. Once detected, the sheath is advanced until the balloon is positioned over the perforation location, aided by fluoroscopy and markers collocated with the expandable member. The expandable member is then expanded, occluding the perforation. The channel or channels formed within the expandable member, depending upon the design and structure (if the expandable member, can allow blood to flow through the channel or channels in the blood vessel until a surgeon can repair the damaged area.

The present disclosure can provide benefits relative to conventional lead removal procedures. Currently, when an accidental perforation is created in a patient's vascular system during a lead removal procedure, there are no methods to quickly stop the bleeding and provide time for a surgeon to go in and repair the vein perforation. Since the balloon is located proximal to the tip of the sheath, it is in a ready position to be inflated to quickly stop the bleeding, continue to allow blood to flow through the vascular system, and provide the surgeon time to prepare for and perform a repair procedure. Allowing blood to keep flowing through the subject's vascular system while simultaneously stopping the bleeding, reduces the likelihood of potentially further harm to the subject through blocked blood flow.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xm, Y1-Yn, and Z1-Zo, the phrase is intended to refer to a single element selected from X, Y, and Z, a combination of elements selected from the same class (e.g., X1 and X2) as well as to combination of elements selected from two or more classes Y1 and Z3).

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

A "load" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

"Eccentric" generally means a non-circular form. For example, when one member is located within another member and the inner member is not located within the geometric center of the outer member, the inner member is considered to be eccentric. For the purposes of this disclosure an "eccentric passageway," "eccentrically shaped passageway," "eccentrically shaped lumen" or other variations, as used herein, shall mean a passageway, particularly a lumen within a sheath or catheter, having a cross sectional opening that is non-circular.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof, shall include all these described in the summary of the invention, brief description of the drawings, detailed description, abstract, and the claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various, aspects, embodiments, and configurations. It is intended neither to identify key or critical elements of the disclosure, not to delineate the scope of the disclosure, but to present selected concepts of the disclosure in a simplified form as an introduction to the more detailed description presented below. As will be appreciated, other aspects, embodiments, and configurations of the disclosure are possible, utilizing alone or in combination, one or more of the features set forth above or described in detail below.

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used, and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
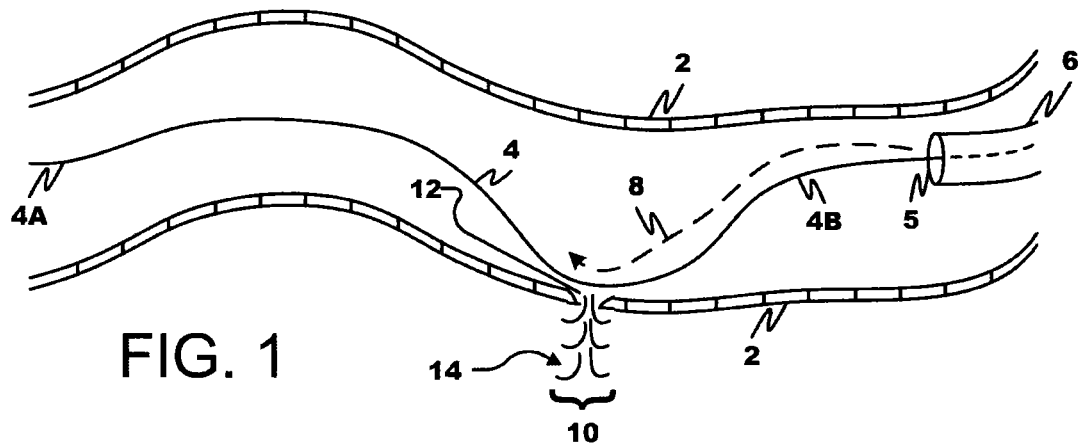
FIG. 1 shows a partial cross section view of a vein with an advancing sheath of a lead removal catheter that accidentally perforates the wall of the vessel.

FIG. 1 shows a partial (cross-sectional view of a vein or other blood vessel with an advancing sheath of a lead removal catheter that accidentally perforates the wall of the vessel. Referring now to FIG. 1, blood vessel 2 terminates at the heart of a patient. Lead 4 lies within the blood vessel 2. Distal end 4A is connected to a surgically implanted device, such as a pacemaker or defibrillator proximal to the patient's heart. Sheath 6 of a lead removal catheter, having been threaded over lead 4, travels along lead 4 from the proximal end 4B of lead 4 in the direction indicated by dashed arrow 8. Lead 4 lies very close to a wall of blood vessel 2 at location 10. In such a situation, as sheath 6 is advanced along lead 4, the tip or cutting instrument of sheath 6 may accidently create a perforation 12 in the wall of blood vessel 2, thereby causing bleeding 14. Factors contributing to the occurrence of the perforation 12 may include: the sharpness or the bend in lead 4; the structural integrity of the wall of vein 2 at location 10; sharp bends in vein 2; the speed or force applied to the lead removal catheter in advancing sheath 6; and/or various combinations of these and other factors known to one skilled in the art.

Figure 2:
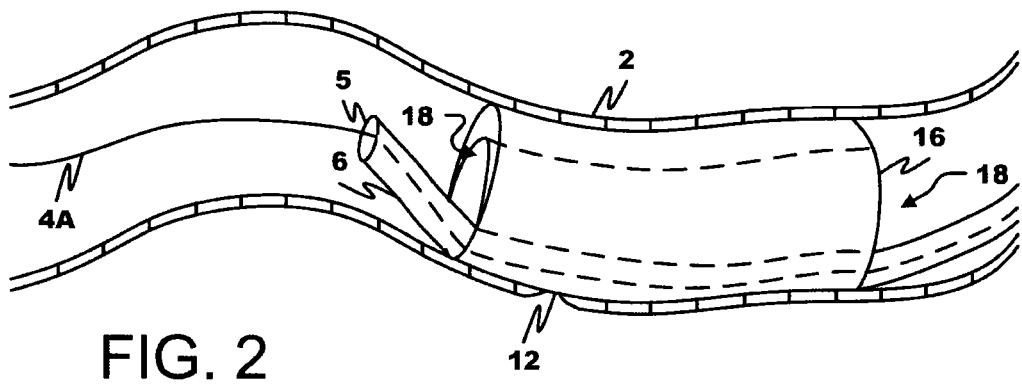
FIG. 2 shows a partial cross section view of the vein of FIG. 1 with the vein perforation occluded by an embodiment of a doughnut-shaped balloon.

FIG. 2 shows a partial cross-sectional view of the blood vessel of FIG. 1 with the perforation at least substantially occluded by an embodiment of an expandable member, such as a balloon. Referring now to FIG. 2, once perforation 12 has been detected with a fluoroscopic device, through monitoring blood pressure, or any other suitable method or means, sheath 6 is advanced farther along lead 4 until expandable member 16, which is attached to a portion of the circumference of sheath 6 and located proximally to distal tip 5 of the sheath 6, is positioned adjacent perforation 12. The position of expandable member 16 can be determined using known techniques, such as one or more radiopaque or other type of imaging markers (not shown) positioned in proximity to or adjacent to expandable member 16. An imaging technique, such as x-ray imaging, magnetic resonance imaging, or ultrasonic imaging, can visually depict relative positions of perforation 12 and expandable member 16. Expandable member 16 is then expanded (e.g., inflated), thereby at least substantially occluding perforation 12 and thus stopping bleeding 14. As will be appreciated, expandable member 16 can include a medication, such as a coagulant (such as NovoSeven™), on an outer surface of the expandable member and/or in an inner volume of the expandable member and released upon member expansion through one or more perforations in the expandable member, thereby potentially accelerating blood clotting. At the same time, blood within blood vessel 2 may flow from one side of expandable member 16 to the other side, thus continuing to flow through blood vessel 2 via a channel 18 (or annulus) formed by the expansion of expandable member 16. As a result, the patient is stabilized, giving the physician time to prep the patient for the procedure to be implemented to permanently repair perforation 12.

Figure 3A:
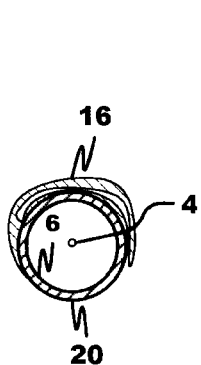
FIG. 3A shows a cross section view of an embodiment of a doughnut-shaped balloon in a deflated position.

FIG. 3A shows a cross-sectional view of an embodiment of an expandable member 16 in a deflated position. Referring to FIG. 3A, expandable member 16 is shown in cross section in a deflated or unexpanded position. Expandable member 16 is attached to or otherwise engages sheath 6 at adhesion area 20 which runs along a substantial length of expandable member 16 and catheter sheath 6 through methods known by those skilled in the art. The bulk of expandable member 16 is folded on itself and wrapped around sheath 6 as shown.

Figure 3B:
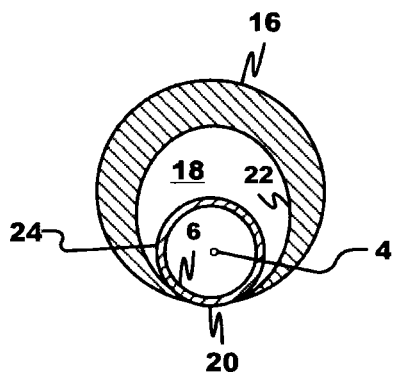
FIG. 3B shows a cross section view of the embodiment of a doughnut-shaped balloon of FIG. 3A in an inflated position.

FIG. 3B shows a cross-sectional view of the embodiment of expandable member 16 of FIG. 3A in an inflated or expanded position. Referring to FIG. 3B, expandable member 16 is shown in cross section in an expanded position. In the expanded position, channel 18 is formed by inner surface 22 of expandable member 16 and outer surface 24 of sheath 6. As illustrated in this figure, the cross section of channel 18 has an eccentric shape. The eccentric shape of the cross section of channel 18 is a result of gluing, welding, bonding, or through any other suitable attachment means, a linear length of expandable member 16 to sheath 6. Thus, blood will continue to flow in blood vessel 2 via channel 18 that is formed after expansion of expandable member 16.

Figure 4A:
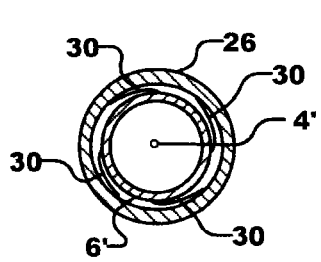
FIG. 4A shows a cross section view of another embodiment of a doughnut-shaped balloon in a deflated position.

FIG. 4A shows a cross-sectional view of another embodiment of an expandable member, configured as a doughnut-shaped balloon, in a deflated position. Referring to FIG. 4A, expandable member 26 is shown in cross section in a deflated position. Expandable member 26 is attached to sheath 6' via four flexible connecting members 30. Less than four flexible connecting members 30, such as two or three, may also be used, as well as more than four flexible connecting members 30, such as five or more.

Figure 4B:
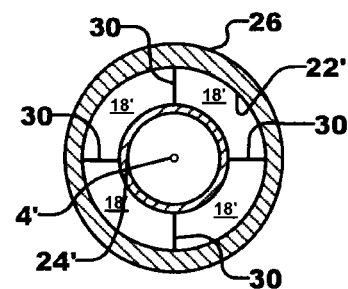
FIG. 4B shows a cross section view of the embodiment of the doughnut-shaped balloon of FIG. 4A in an inflated position.
Figure 5:
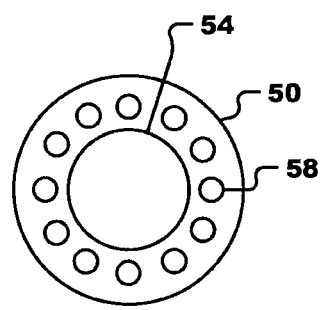
FIG. 5 shows the cross section of the distal end of a known prior art laser catheter.

FIG. 4B shows a cross-sectional view of the embodiment of the expandable member of FIG. 4A in an inflated position. Referring now to FIG. 4B, expandable member 26 is shown in cross section in an inflated position. In the inflated position, four channels 18' are formed by the inner surface 22' of expandable member 26, the surfaces of four flexible connecting members 30, and outer surface 24' of the catheter sheath 6'. With two flexible connecting members 30, two channels 18' would be formed. With three flexible connecting members 30, three channels 18' would be formed. With each additional flexible connecting member 30 added, one additional channel 18' will be formed. Thus, blood will continue to flow in blood vessel 2 via one or more channels 18' that are formed after inflation of expandable member 26. Substituting expandable member 26 for expandable member 16 shown in FIGS. 2, 3A, and 3B, expandable member 26 may be used in the same fashion as expandable member 16 described above. Many other configurations and methods for securing an expandable member to the catheter sheath are possible and fall within the scope of this disclosure, though not shown, but well known by one skilled in the art. These include, for example, (1) an expandable braided structure with a sleeve around the braided structure; and (2) memory shaped metal housed within a sleeve that once the sleeve is retracted the memory shaped metal can expand and contact the vessel walls.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. For example, in the foregoing Detailed Description, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspect, embodiment, and configuration. Thus, the following claims are hereby incorporated into this Detailed Description, with each claim, standing on its own as a separate preferred embodiment of the disclosure.

Moreover, though the description of the disclosure has included descriptions of one or more aspects, embodiments, or configurations and certain variations and modifications, other variations, combinations, and modifications are within the scope of the disclosure, e.g., as may be within the skill and knowledge of those in the art, after understanding the present disclosure. It is intended obtain rights include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for occluding a perforation in a blood vessel of a patient, the method comprising:
    detecting the perforation in the blood vessel;
    advancing a sheath carrying an inflatable balloon in a deflated state in the blood vessel,
        wherein the sheath comprises a lumen receiving a lead, and an outer surface having a length and a circumference,
        wherein the inflatable balloon is only coupled to a portion of the circumference along the length of the outer surface of the sheath,
        wherein advancing the sheath comprises advancing the sheath over the lead disposed in the lumen until the inflatable balloon is substantially adjacent to the perforation in the blood vessel;
    radially expanding the inflatable balloon in the blood vessel to an inflated state, thereby at least substantially occluding the perforation in the blood vessel, whereupon radially expanding the inflatable balloon, (i) a channel is formed between an inner surface of the inflatable balloon and an outer surface of the sheath, wherein the channel comprises an eccentrically shaped cross section and (ii) a cross section of the inflatable balloon comprises an eccentric shape, wherein the eccentric shape is defined by a section between the inner surface of the inflatable balloon and an outer surface of the balloon; and
    removing the lead from the patient using the lumen of the sheath, wherein the perforation is formed in the course of removing the lead from the patient, wherein the lead is or was attached to one of a pacemaker and defibrillator, and wherein the sheath is advanced over the lead prior to detecting the perforation in the blood vessel.

2. The method of claim 1, whereupon radially expanding the inflatable balloon and forming the channel permits blood to flow through the channel from a first side to a second side of the inflatable balloon.

3. The method of claim 1, wherein detecting the perforation in the blood vessel comprises using fluoroscopy to detect the perforation.

4. The method of claim 1, wherein the inflatable balloon comprises and/or releases a coagulant to facilitate blood clotting in the perforation in the blood vessel.

5. The method of claim 1, wherein the inflatable balloon comprises at least one imaging marker, and further comprising determining location of the inflatable balloon within the patient by determining the location of the at least one imaging marker.

6. The method of claim 5, wherein the at least one imaging marker comprises at least one of a radiopaque and radiolucent material.

7. The method of claim 1, wherein the inflatable balloon is coupled to the length of the outer surface of the sheath by gluing, welding, or bonding.

\* \* \* \* \*